United States Patent
Marhold et al.

(10) Patent No.: US 6,420,601 B2
(45) Date of Patent: Jul. 16, 2002

(54) PROCESS FOR THE PREPARATION OF 3,5-BIS(TRIFLUORO-METHYL)-BENZOYL CHLORIDES AND NOVEL 3,5-BIS(TRI-HALOGENOMETHYL)-AND 3,5-DIMETHYLBENZOYL HALIDES

(75) Inventors: Albrecht Marhold, Leverkusen; Jörn Stölting, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/769,797

(22) Filed: Jan. 25, 2001

(30) Foreign Application Priority Data

Feb. 3, 2000 (DE) .......................... 100 04 717

(51) Int. Cl.$^7$ .............................. C07C 51/58
(52) U.S. Cl. ................ 562/840; 562/852; 562/849; 562/861; 562/864; 562/493
(58) Field of Search ................ 562/849, 852, 562/861, 864, 493, 840

(56) References Cited

U.S. PATENT DOCUMENTS 4,500,471 A * 2/1985 Cotter et al. ............ 260/544 D

FOREIGN PATENT DOCUMENTS

| DE | 707955 | * | 4/1941 |
| FR | 820696 | * | 11/1937 |

OTHER PUBLICATIONS

Davies et al, Journal of Chemistry Society, vol. 121, pp. 2202–2215, 1922.*
J. Med. Chem. (month unavailable) 1995, 38, pp. 3106–3120, Natsugari et al, Novel, Potent, And Orally Active Substance P Antagonists: Synthesis and Antagonist Activity of N–Benzylcarboxamide Derivatives of Pyridol[3, 4]pyridine.
Bull. Soc. Chim. Fr. (month unavailable), 1962, pp. 587–593, J. Lictenberger et F. Weiss, —Sur les dérivés du phényfluoroforme. 1. —Les trifluorométhyl–benzophénones.
J. Med. Chem. (month unavailable) 1995, 38, pp. 3106–3120, Natsugari et al, Novel, Potent, And Orally Active Substance P Antagonists: Synthesis and Antagonist Activity of N–Benzylcarboxamide Derivatives of Pyridol[3, 4b]pyridine.

Journal of Organic Chemistry, Bd. 41, Nr. 13, (month unavailable) 1976, Seiten 2256–2258, XP002164253, Letzte Reaktion, Seite 2257, Rechte Spalte, T. S. Croft et al, "Reduction of Perfluoroacyl Halides with Organosilison Hydrides. A Direct Synthesis of Fluorine Containing Esters and Lactones".*

J. Org. Chem., 24, Sep. 1959, pp. 1301–1309, H. A. Smith, C.A. Buehler, T.A. Magee, K.V. Nayak and D.M. Glenn, Physiologically Active Compounds, III. Hydrochlorides of Amino Esters of Phenyclyclohexylglycolic Acids, of Amides of Benzilic, Phenylcyclohexyl–and Dicyclohexylglycolic, and Phenylcyclohexylacetic Acids; 2–Methylthioethyl Ester Methiodides of Substituted Benzilic Acids.

Synlett; Dec. 1990, pp. 747–748, Manfred Schlosser, Georges Katsoulos, Sadahito Takagishi, Superbase Reactions: The Expedient and Selective Metalation of Fluorine–or Trifluoromethyl–Substituted Benzenes.

Journal of. Organometallic Chemistry, 67, (month unavailable) 1974) pp. 321–325, Paul Aeberli and William J. Houlihan, The Metalation of 1,3–Bis(Trifluoromethyl)Benzene by n–Butyllithium.

Canadian Journal of Chemistry, vol. 41, (month unavailable) 1963, pp. 2962–2968, Antineoplastic Agents IX. N–Benzyl–N–Bis(2–Haloethyl)Amines, Gerorge R. Pettit, David S. Blonda and Ernest C. Harrington.

* cited by examiner

*Primary Examiner*—Paul J. Killos
*Assistant Examiner*—Hector M Reyes
(74) *Attorney, Agent, or Firm*—Joseph C. Gil; Richard E. L. Henderson

(57) ABSTRACT

3,5-Bis(trifluoromethyl)benzoyl chlorides optionally substituted with fluorine or chlorine are advantageously prepared by converting 3,5-dimethylbenzoic acids optionally substituted with fluorine or chlorine into the corresponding acid chlorides; completely free-radically chlorinating said chlorides in the side chains, giving 3,5-bis(trichloromethyl) benzoyl chlorides optionally substituted by fluorine or chlorine; fluorinating the latter with anhydrous hydrogen fluoride and/or antimony pentafluoride, giving 3,5-bis (trifluoromethyl)benzoyl fluorides optionally substituted with fluorine or chlorine; and then reacting the 3,5-bis (trifluoromethyl)benzoyl fluorides with silicon tetrachloride in the presence of a further Lewis acid. Some of the 3,5-bis(trihalogenomethyl) and 3,5-dimethylbenzoyl halides which arise as intermediates are novel compounds.

12 Claims, No Drawings

PROCESS FOR THE PREPARATION OF 3,5-BIS(TRIFLUORO-METHYL)-BENZOYL CHLORIDES AND NOVEL 3,5-BIS(TRI-HALOGENOMETHYL)-AND 3,5-DIMETHYLBENZOYL HALIDES

BACKGROUND OF THE INVENTION

The present invention relates to a process for the preparation of 3,5-bis-(trifluoromethyl)benzoyl chlorides from the corresponding 3,5-dimethylbenzoic acids and to novel 3,5-bis(trihalogenomethyl)- and 3,5-dimethylbenzoyl halides that arise as intermediates in the process. In the text below, 3,5-bis(trifluoromethyl)benzoyl chlorides are also referred to as BTBs.

BTBs are intermediates for the preparation of pharmaceutical and agrochemical active ingredients and photoresist compositions.

The preparation of BTBs from the corresponding 3,5-bis (trifluoromethyl)benzoic acid by chlorination is known (see, for example, J. Med. Chem., 38, 3106 (1995)). This acid can be obtained in two different ways, by (a) metallizing 1-bromo-3,5-bis(trifluoromethyl)benzene with magnesium or lithium (see Bull. Soc. Chim. Fr., 1962 (587) and Chem. Ber., 129, 233 (1996)) and then reacting with carbon dioxide or, in the presence of a palladium catalyst, with carbon monoxide and water (see JP-OS 09/67,297) or (b) reacting 3,5-bis(trifluoromethyl)benzene with a mixture of butyllithium and potassium t-butoxide (see Synlett, 1990, 747) or only with butyllithium (see J. Organomet. Chem., 67, 321 (1974)) and then with carbon dioxide.

These processes for the preparation of BTBs are less suitable for the industrial scale because in all cases organometallic compounds have to be prepared and handled, which is possible only with great technological expenditure. Moreover, 3,5-bis(trifluoromethyl)benzene and the corresponding 1-bromo compound can be prepared only by a complex route. Added to this is the danger of the exothermic decomposition of meta-trifluoromethyl-substituted phenylmagnesium and -lithium compounds, which likewise require great expenditure for somewhat reliable control.

It is also known that 3,5-bis(trifluoromethyl)benzoyl fluorides can be prepared by selectively hydrolyzing 1,3,5-tris (trichloromethyl)benzenes with water to give 3,5-bis (trichloromethyl)benzoyl chlorides (see German Patent Specification 705,650) and then carrying out a complete chlorine/fluorine exchange with hydrogen fluoride or antimony trifluoride (see German Patent Specification 707,955). Whether and, where appropriate, how the corresponding benzoyl chlorides ("BTBs") can be obtained from 3,5-bis- (trifluoromethyl)-benzoyl fluorides is not known.

There is therefore a need for a process for the preparation of BTBs that can be reliably carried out on an industrial scale without particular complexity and that starts from readily accessible starting materials.

SUMMARY OF THE INVENTION

We have now found a process for the preparation of 3,5-bis(trifluoromethyl)benzoyl chlorides of formula (I)

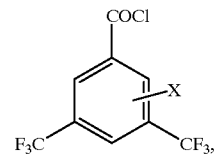

(I)

wherein
X is hydrogen, fluorine, or chlorine, comprising
(1) converting 3,5-dimethylbenzoic acids of formula (V)

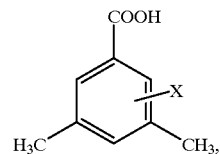

(V)

wherein
X has the meaning given for formula (I),
into the corresponding acid chlorides of formula (IV)

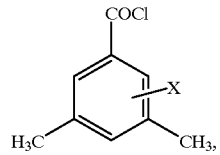

(IV)

wherein
X has the meaning given for formula (I),
(2) completely free-radically chlorinating the acid chlorides of formula (IV) in the side chains to give 3,5-bis (trichloromethyl)benzoyl chlorides of formula (III)

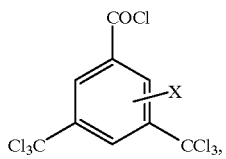

(III)

wherein
X has the meaning given for formula (I),
(3) fluorinating the 3,5-bis(trichloromethyl)benzoyl chlorides of formula (III) with anhydrous hydrogen fluoride and/or antimony pentafluoride to give 3,5-bis (trifluoromethyl)benzoyl fluorides of formula (II)

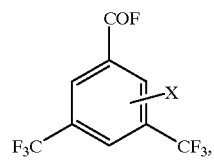

(II)

wherein

X has the meaning given for formula (I), and (4) reacting the 3,5-bis(trifluoromethyl)benzoyl fluorides of formula (II) with silicon tetrachloride in the presence of a further Lewis acid to give the compounds of formula (I).

In formulas (I) to (V), X is preferably hydrogen.

DETAILED DESCRIPTION OF THE INVENTION

The first stage of the process according to the invention, the preparation of the acid chlorides of the formula (IV) from the benzoic acids (V), can be carried out analogously to known processes for the preparation of carbonyl chlorides from carboxylic acids. One possibility for the reaction of 3,5-dimethylbenzoic acid with phosphorus pentachloride is known from Can. J. Chem., 41, 2962 (1963) and another with thionyl chloride is known from J. Org. Chem., 24, 1301 (1959). These reactions can be carried out analogously for compounds in which X is fluorine or chlorine. The benzoic acids of the formula (V) required to carry out the first stage can be prepared by known processes or analogously thereto. 3,5-Dimethylbenzoic acid is commercially available.

The conversion to the acid halides of the formula (IV) can be carried out with chlorinating reagents, for example, with thionyl chloride, phosphorus trichloride, phosphorus pentachloride, phosphorus oxychloride, oxalyl chloride or phosgene. Preference is given to using thionyl chloride or oxalyl chloride, the reaction products of which (hydrogen chloride and sulfur dioxide or hydrogen chloride, carbon monoxide and carbon dioxide respectively) are readily volatile and therefore can be removed easily.

The conversion to the acid chlorides of formula (IV) is preferably carried out in the presence of a diluent. Suitable for this purpose are inert organic solvents or mixtures thereof. By way of example, mention may be made of aliphatic, alicyclic, and aromatic hydrocarbons, such as petroleum ether, hexane, heptane, cyclohexane, methylcyclohexane, benzene, toluene, xylenes and Decalin, halogenated hydrocarbons, such as chlorobenzene, dichlorobenzenes, methylene chloride, chloroform, tetrachloromethane, dichloroethane, trichloroethane and tetrachloroethylene, ethers, such as diethyl ether, tetrahydrofuran, 1,2-dimethoxyethane, 1,2-diethoxyethane, diethylene glycol dimethyl ether and anisole, esters, such as methyl acetate, ethyl acetate and butyl acetate, and sulfones, such as sulfolane. Per mole of benzoic acid of the formula (V), 50 to 150 ml of diluent, for example, can be used.

It is advantageous to use an excess of the chlorinating reagent, for example, 1.1 to 10 mol (preferably 1.2 to 3 mol) of chlorinating reagent per mole of the benzoic acid of the formula (V).

The reaction temperature for this stage can be varied within a relatively wide range. For example, it can be between 0 and 150° C., preferably between 20 and 120° C.

The work-up following the reaction can, for example, be carried out by distillation. If the preferred chlorinating reagents are used, it is possible to readily distill off their excess and the diluent which may be present, and to use the distillation residue as crude product in the next stage.

The second stage of the process according to the invention, the side-chain chlorination of the 3,5-dimethylbenzoyl chlorides of the formula (IV), is novel. This side-chain chlorination is carried out as a free-radical reaction. This can be achieved as a result of elevated temperature, irradiation by a light source, and/or addition of a free-radical initiator. Examples of suitable light sources are incandescent lamps, preferably halogen lamps and medium- and high-pressure mercury vapour lamps. Suitable free-radical initiators are, for example, benzoyl peroxide, di-tert-butyl peroxide, 2,2-aza-bis(isobutyronitrile), and 2-phenylazo-2,4-dimethyl-4-methoxy-valeronitrile. Preference is given to using a light source at elevated temperature. The reaction temperature can, for example, be between 80 and 250° C., preferably 100 to 220° C., particularly preferably between 110 and 190° C. Here, it is advantageous to start the chlorination at relatively low temperatures, for example, 80 to 140° C., and to continue to the end at relatively high temperatures, for example, 160 to 250° C.

The chlorinating agent used in this stage is generally elemental chlorine.

Per mole of dimethylbenzoyl chloride of the formula (IV), it is possible, for example, to use 6.3 to 18 mol (preferably 7.2 to 12 mol) of chlorine gas.

For work-up after the reaction it is possible to displace any excess chlorine, e.g., by introducing an inert gas, such as nitrogen, or by applying a vacuum. Crude product obtainable in this way can be used directly in the next reaction stage, although, if desired, it can also be purified, e.g., by vacuum distillation.

The third stage of the process according to the invention is the fluorination of the 3,5-bis(trichloromethyl)benzoyl chlorides of the formula (III) to give the 3,5-bis(trifluoromethyl)benzoyl fluorides of the formula (II). One possibility for the preparation of the 3,5-bis(trifluoromethyl) benzoyl fluoride is already known from German Patent Specification 707,955 and can be transferred analogously to the compounds in which X is fluorine or chlorine.

The fluorination is carried out with anhydrous hydrofluoric acid and/or antimony pentafluoride. In some instances, catalysts may be added, e.g., Lewis acids, such as titanium tetrachloride, boron trichloride, or antimony pentafluoride, which generally increases the rate of the reaction. Preference is given to using anhydrous hydrogen fluoride in a mixture with titanium tetrachloride. It is also possible to add the Lewis acids after the reaction has started.

Per mole of benzoyl chloride of the formula (III), it is possible to use, for example, 7.7 to 21 mol (corresponding to a 10 to 200% excess) of anhydrous hydrogen fluoride or the corresponding amount of antimony pentafluoride and, for example, 0 to 0.2 mol of Lewis acids.

The fluorination can be carried out, for example, by starting at a temperature below the boiling point (at atmospheric pressure) of hydrogen fluoride, for example, at −20 to +15° C., and, to complete the reaction, continuing to the end at relatively high temperatures, for example, at 100 to 180° C. As the result of the vapor pressure of the hydrogen fluoride, pressures up to 100 bar can arise here, which necessitates the use of reaction vessels which are appropriately pressure-resistant. The hydrogen chloride liberated is decompressed, for example, at temperatures above +20° C. via a pressure relief valve.

The reaction mixture that is present following the fluorination can be worked up by fractional distillation, for example.

The final fourth stage of the process according to the invention is the chlorine/fluorine exchange at the carbonyl group, which has hitherto not been disclosed for these compounds. This is carried out using silicon tetrachloride as reagent in the presence of a further Lewis acid, for example, aluminum chloride, boron trifluoride, titanium tetrachloride, iron trichloride, or mixtures thereof.

Per mole of benzoyl fluoride of the formula (II), it is possible, for example, to use 0.25 to 1 mol (1 to 4 equivalents), preferably 0.3 to 0.5 mol, of silicon tetrachloride, and 0.01 to 0.1 mol, preferably 0.02 to 0.05 mol, of further Lewis acid.

This chlorine/fluorine exchange can, for example, be carried out at temperatures between 0 and 70° C., preferably between 20 and 50° C. The procedure here may involve initially introducing the further Lewis acid either with the benzoyl fluoride of the formula (II) or with the silicon tetrachloride and metering in the other component in each case. In this way, the evolution of gas can be controlled easily.

The reaction mixture which is present following the chlorine/fluorine exchange can be worked up, for example, by firstly separating off the solid constituents, e.g., by filtration, preferably following the addition of a filtration auxiliary, such as cellulose or a zeolite. By fractional vacuum distillation of the filtrate it is possible to obtain the prepared BTB in pure form. To deactivate residues of the silicon tetrachloride and/or the further Lewis acid, it may be advantageous to add a small amount of an aryl- or alkylphosphine, for example, 0.1 to 1% by weight, to the mixture to be distilled. Triphenylphosphine, for example, is suitable for this purpose.

Using the process according to the invention, BTBs of the formula (I) can be prepared in good yields from the readily accessible 3,5-dimethylbenzoic acids of the formula (V) in a process which can be readily and easily carried out on an industrial scale. Viewed over all reaction stages, the yield is significantly greater than 60% of theory.

Some of the compounds of the formulas (I) to (IV) are novel. The present invention therefore also relates to 3,5-bis(trifluoromethyl)benzoyl chlorides of the formula (Ia)

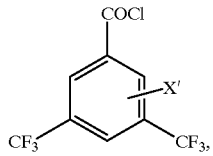

(Ia)

in which

X' is fluorine or chlorine, 3,5-bis(trifluoromethyl)benzoyl fluorides of the formula (IIa)

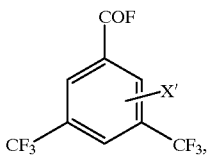

(IIa)

in which

X' is fluorine or chlorine, 3,5-bis(trichloromethyl)benzoyl chlorides of the formula (IIIa)

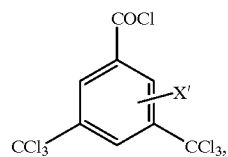

(IIIa)

in which

X' is fluorine or chlorine, and 3,5-dimethylbenzoyl chlorides of the formula (IVa)

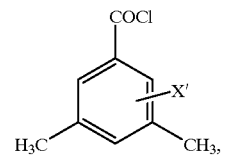

(IVa)

in which

X' is fluorine or chlorine.

The preparation of compounds of the formulas (Ia) to (IVa) is described above. They are novel intermediates for the advantageous preparation of 3,5-bis(trifluoromethyl)benzoyl chloride by the process according to the invention.

EXAMPLES

Example 1

3,5-Dimethylbenzoyl chloride

A 4 liter flat-flange reaction vessel was initially charged with 1000 g of 3,5-dimethylbenzoic acid in 450 ml of toluene, and, with stirring at 60° C., 80 ml of thionyl chloride were added dropwise over the course of 2 hours, a gas being evolved. The mixture was then heated to boiling (internal temperature 102° C.) and refluxed for 2 hours. Then, over the course of 1.5 hours, excess thionyl chloride and some of the toluene were distilled off up to a head temperature of 102° C. at atmospheric pressure. The mixture was left to cool to 80° C., and the toluene was distilled off, now at 20 mbar. Residual amounts were removed by distillation over a column at 20 mbar up to the boiling point of 110° C. (in the still). The residue obtained was 1092 g (96.7% of theory) of 3,5-dimethylbenzoyl chloride.

Example 2

3,5-Bis(trichloromethyl)benzoyl chloride

A reaction vessel equipped with an air-cooled UV immersion lamp was initially charged, at 120° C., with 1092 g of 3,5-dimethylbenzoyl chloride, and a total of 4340 g of chlorine were introduced over 61 hours with UV irradiation and a steady temperature increase to 180° C. According to GC analysis, 100% of the starting material had then reacted. After the excess of chlorine had been blown out with nitrogen, 2390 g (98.1% of theory) of 3,5-bis(trichloromethyl)benzoyl chloride were left behind.

Example 3

3,5-Bis(trifluoromethyl)benzoyl fluoride

A 5 liter stainless steel stirred autoclave with inclined condenser (operated with a coolant at a temperature of −10°

C.) and pressure regulator was initially charged with 990 ml of anhydrous hydrofluoric acid. Then, 1126 g of 3,5-bis (trichloromethyl)benzoyl chloride were added dropwise over 30 minutes at −5 to 0° C., the evolution of hydrogen chloride gas being only weak. The temperature was allowed to increase to +20° C. When the slight evolution of gas had stopped (after 1.5 hours), 68 g of titanium tetrachloride were added over 40 minutes. After the renewed evolution of gas had subsided (after 2 hours), the apparatus was sealed, nitrogen was injected to 10 bar, and the apparatus was heated in stages to 140° C., the hydrogen chloride produced being continuously decompressed at 25 bar. After 11 hours at 140° C. the reaction was complete. The autoclave was cooled and decompressed, and the excess hydrogen fluoride was distilled off at atmospheric pressure (248 g), and the residue was distilled under reduced pressure (70 to 12 mbar) over a bridge (maximum head temperature: 84° C. at 12 mbar). 43 g of a resinous residue remained. The crude distillate was fractionally distilled under reduced pressure over a 60 cm column packed with Wilson spirals (50 mbar, 140° C. bath temperature, 75° C. head temperature). In addition to 105 g of distillation residue (not fully fluorinated products which can be used again), 633 g (81% of theory) of 3,5-bis (trifluoromethyl)benzoyl fluoride with a purity of 99.9% (GC, area %) were obtained.

Example 4

3,5-Bis(trifluoromethyl)benzoyl chloride 1040 g of 3,5-bis(trifluoromethyl)benzoyl fluoride and 24 g of aluminum chloride were initially introduced and heated to 40° C. With stirring, 224 g of silicon tetrachloride were added dropwise over 3 hours, where the temperature was controlled and did not exceed 45° C. The mixture was then stirred until the evolution of gas had stopped (2 hours). 30 g of zeolite X133 were then added, and the mixture was filtered. This gave 1000 g of a cloudy filtrate, which was admixed with 5 g of triphenylphosphine and distilled at 12 mbar over a 70 cm column. This gave 623 g (83.6% of theory) of 3,5-bis(trifluoromethyl)benzoyl chloride which passed over at 68° C. (bath temperature: 80° C.).

Example 5

A stirred apparatus with gas feed and discharge to an eliminator was initially charged with 100 g (0.593 mol) of 3,5-dimethylbenzoyl chloride together with 0.5 g of iron (III) chloride, and 42 g of chlorine were introduced at 22–28° C. over the course of 3 hours. Fractional distillation gave 78 g of 2-chloro-3,5-dimethylbenzoyl chloride. Boiling range: 113–114° C. at 5 mbar.

Example 6

A chlorination apparatus fitted with a UV irradiation lamp was initially charged with 78 g of 2-chloro-3,5-dimethylbenzoyl chloride in 100 ml of dry 4-chlorobenzotrifluoride, and 1 g of phosphorus trichloride and 0.5 g of potassium chloride were added. The temperature was initially set at 100° C., and chlorine was slowly introduced. Over the course of the chlorination, the internal temperature was increased to solvent reflux. After 20 hours, 200 g of chlorine had been introduced, and the reaction mixture was fractionally distilled. 119 g of 2-chloro-3,5-bistrichloromethylbenzoyl chloride passed over in the boiling range 145–147° C. at 0.2 mbar.

$n_D^{20}$:1.6025

Example 7

An autoclave made of stainless steel was charged with 100 ml of HF and 2 ml of antimony pentachloride. At 0° C., a solution of 119 g of 2-chloro-3,5-bistrifluoromethylbenzoyl chloride in 50 ml of dry dichloromethane was metered in. Nitrogen was then injected to 10 bar, and then the temperature was increased in stages to 145° C. The hydrogen chloride which formed was decompressed via a reflux condenser cooled to −15° C. at 25 bar. After 9 hours, the evolution of hydrogen chloride had stopped, and the system was cooled to room temperature. Hydrogen fluoride that was still present and dichloromethane were distilled off. The reaction product was subjected to fine distillation. 68 g of 2-chloro-3,5-bistrifluoromethylbenzoyl fluoride passed over in the boiling range 76–77° C. at 13 mbar.

$n_D^{20}$:1.4292

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of 3,5-bis (trifluoromethyl)benzoyl chlorides of formula (I)

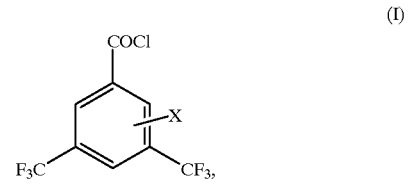

wherein

X is hydrogen, fluorine, or chlorine, comprising (1) converting 3,5-dimethylbenzoic acids of formula (V)

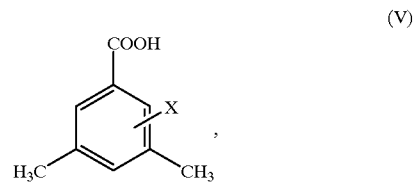

wherein

X has the meaning given for formula (I), into the corresponding acid chlorides of formula (IV)

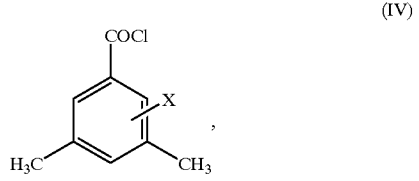

wherein

X has the meaning given for formula (I), (2) completely free-radically chlorinating the acid chlorides of formula (IV) in the side chains to give 3,5-bis (trichloromethyl)benzoyl chlorides of formula (III)

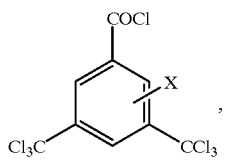

(III)

wherein
X has the meaning given for formula (I), (3) fluorinating the 3,5-bis(trichloromethyl)benzoyl chlorides of formula (III) with anhydrous hydrogen fluoride and/or antimony pentafluoride to give 3,5-bis(trifluoromethyl)benzoyl fluorides of formula (II)

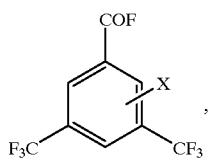

(II)

wherein
X has the meaning given for formula (I), and (4) reacting the 3,5-bis(trifluoromethyl)benzoyl fluorides of formula (II) with silicon tetrachloride in the presence of a further Lewis acid to give the compounds of the formula (I).

2. A process according to claim 1 wherein the conversion to the acid chlorides of formula (IV) is carried out with a chlorinating reagent selected from the group consisting of thionyl chloride, phosphorus trichloride, phosphorus pentachloride, phosphorus oxychloride, oxalyl chloride, and phosgene, and in the presence of the diluent.

3. A process according to claim 1 wherein 1.1 to 10 mol of chlorinating reagent, per mole of the benzoic acid of the formula (V), are used and wherein the operating temperature is 0 to 150° C.

4. A process according to claim 1 wherein the free-radical side-chain chlorination is carried out at elevated temperature with elemental chlorine using irradiation by a light source and/or the addition of a free-radical initiator at 80 to 250° C.

5. A process according to claim 1 wherein 7.2 to 12 mol of chlorine gas are used per mole of dimethylbenzoyl chloride of the formula (IV).

6. A process according to claim 1 wherein the fluorination is carried out using 7.7 to 21 mol of anhydrous hydrogen fluoride per mole of benzoyl chloride of the formula (III) with the addition of a Lewis acid.

7. A process according to claim 1 wherein the reaction with silicon tetrachloride is carried out in the presence of aluminum chloride, boron trifluoride, titanium tetrachloride, iron trichloride, or mixtures thereof.

8. A process according to claim 1 wherein the reaction with silicon tetrachloride is carried out with 0.25 to 1 mol of silicon tetrachloride and 0.01 to 0.1 mol of further Lewis acid, in each case based on 1 mol of benzoyl fluoride of the formula (II).

9. 3,5-Bis(trifluoromethyl)benzoyl chlorides of the formula (Ia)

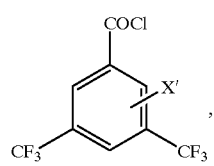

(Ia)

wherein
X' is fluorine or chlorine.

10. 3,5-Bis(trifluoromethyl)benzoyl fluorides of the formula (IIa)

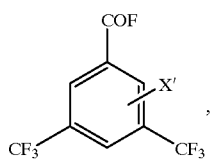

(IIa)

wherein
X' is fluorine or chlorine.

11. 3,5-Bis(trichloromethyl)benzoyl chlorides of the formula (IIIa)

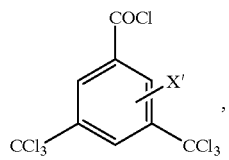

(IIIa)

wherein
X' is fluorine or chlorine.

12. 3,5-Dimethylbenzoyl chlorides of the formula (IVa)

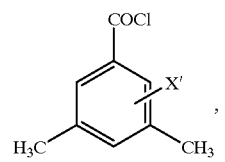

(IVa)

wherein
X' is fluorine or chlorine.

* * * * *